US00RE49221E

(19) United States
(12) Reissued Patent
Schick et al.

(10) Patent Number: US RE49,221 E
(45) Date of Reissued Patent: Sep. 27, 2022

(54) SINGLE-USE MANIFOLDS FOR AUTOMATED, ASEPTIC HANDLING OF SOLUTIONS IN BIOPROCESSING APPLICATIONS

(71) Applicant: Parker Intangibles, LLC, Cleveland, OH (US)

(72) Inventors: Karl G. Schick, Stoughton, WI (US); David A. Uhen, Burlington, WI (US)

(73) Assignee: Parker Intangibles, LLC, Cleveland, OH (US)

(21) Appl. No.: 16/456,170

(22) Filed: Jun. 28, 2019

Related U.S. Patent Documents

Reissue of:
(64) Patent No.: 9,700,844
Issued: Jul. 11, 2017
Appl. No.: 13/769,971
Filed: Feb. 19, 2013

U.S. Applications:
(60) Continuation of application No. 11/294,297, filed on Dec. 5, 2005, now Pat. No. 9,283,521, which is a
(Continued)

(51) Int. Cl.
*B01D 61/20* (2006.01)
*B01D 15/10* (2006.01)
(Continued)

(52) U.S. Cl.
CPC ..... *B01D 61/20* (2013.01); *B01D 15/10* (2013.01); *B01D 61/18* (2013.01); *B01D 61/22* (2013.01);
(Continued)

(58) Field of Classification Search
CPC ..... B01D 61/22; B01D 15/10; B01D 61/20; B01D 61/18; B01D 15/247;
(Continued)

(56) References Cited

U.S. PATENT DOCUMENTS 2,254,400 A 9/1941 Starr
2,769,140 A 10/1956 Obenshain
(Continued)

FOREIGN PATENT DOCUMENTS

DE 197 20 504 A1 11/1998
EP 654664 A2 5/1995
(Continued)

OTHER PUBLICATIONS

International Search Report and Written Opinion for PCT Application No. PCT/US2006/061561, dated Jun. 4, 2007.
(Continued)

*Primary Examiner* — Krisanne M Jastrzab
*Assistant Examiner* — Elizabeth L McKane
(74) *Attorney, Agent, or Firm* — Cook Alex, Ltd.

(57) ABSTRACT

Presteralized manifolds are provided which are designed for sterile packaging and single-use approaches. Disposable tubing and flexible-wall containers are assembled via aseptic connectors. These manifolds are adapted to interact with other equipment which can be operated by a controller which provides automated and accurate delivery of biotechnology fluid. The manifold also can be used in conjunction with one or more sensors such as pressure and conductivity sensors that interact with the controller or are connected to a separate user interface. An aseptic environment obtains avoiding or reducing cleaning and quality assurance procedures.

38 Claims, 6 Drawing Sheets

Related U.S. Application Data continuation-in-part of application No. 10/764,624, filed on Jan. 15, 2004, now Pat. No. 7,052,603, which is a division of application No. 10/172,082, filed on Jun. 14, 2002, now Pat. No. 6,712,963.

(51) Int. Cl.

| | |
|---|---|
| ***B01D 61/18*** | (2006.01) |
| ***B01D 61/22*** | (2006.01) |
| ***B01D 15/14*** | (2006.01) |
| ***B01D 15/24*** | (2006.01) |
| ***G01N 27/10*** | (2006.01) |
| ***G01N 30/88*** | (2006.01) |

(52) U.S. Cl.

CPC ..... *B01D 15/14* (2013.01); *B01D 15/247* (2013.01); *B01D 2311/06* (2013.01); *B01D 2313/50* (2013.01); *B01D 2313/58* (2013.01); *G01N 27/10* (2013.01); *G01N 2030/8813* (2013.01)

(58) Field of Classification Search

CPC ..... B01D 2313/58; B01D 2313/50; B01D 15/14; B01D 2311/06; B01D 2311/2649; G01N 2030/8813; G01N 27/10

See application file for complete search history.

(56) References Cited

U.S. PATENT DOCUMENTS 3,447,070 A 5/1969 Sand et al.
3,743,581 A 7/1973 Cady et al.
4,010,715 A 3/1977 Robar et al.
4,147,596 A 4/1979 Baboian et al.
4,227,151 A 10/1980 Ellis et al.
4,301,414 A 11/1981 Hill et al.
4,303,887 A 12/1981 Hill et al.
4,399,362 A 8/1983 Cormier et al.
4,399,462 A 8/1983 Balopole et al.
4,433,973 A 2/1984 Kurtz et al.
4,484,599 A 11/1984 Hanover et al.
4,513,248 A 4/1985 Miller
4,626,346 A 12/1986 Hall
4,648,043 A 3/1987 O'Leary
4,680,109 A 7/1987 Yamada et al.
4,713,051 A 12/1987 Steppe et al.
4,740,755 A 4/1988 Ogawa
4,818,384 A 4/1989 Mayer
4,859,078 A 8/1989 Bowman et al.
5,076,931 A 12/1991 Muller
5,107,908 A 4/1992 Newhouse et al.
5,112,489 A 5/1992 Hartmann
5,200,090 A 4/1993 Ford et al.
5,207,642 A 5/1993 Orkin et al.
5,231,867 A 8/1993 Serwatzky
5,256,294 A 10/1993 van Reis
5,273,517 A 12/1993 Barone et al.
5,282,787 A 2/1994 Wortrich
5,282,972 A 2/1994 Hanna et al.
5,328,584 A 7/1994 Erickson et al.
5,340,290 A 8/1994 Clemens
5,350,290 A 9/1994 Honings
5,369,264 A 11/1994 Rosa et al.
5,384,028 A 1/1995 Ito
5,421,983 A 6/1995 Slack et al.
5,431,811 A 7/1995 Tusini et al.
5,435,170 A 7/1995 Voelker et al.
5,455,513 A 10/1995 Brown et al.
5,480,063 A 1/1996 Keyes et al.
5,480,393 A 1/1996 Bommarito
5,518,933 A 5/1996 Ishibashi
5,520,816 A 5/1996 Kuepper
5,538,405 A 7/1996 Patno et al.
5,589,076 A 12/1996 Womack
5,597,486 A 1/1997 Lutz
5,599,447 A 2/1997 Pearl et al.
5,608,200 A 3/1997 Le Goff et al.
5,680,960 A 10/1997 Keyes et al.
5,686,309 A 11/1997 Frank et al.
5,693,229 A 12/1997 Hartmann
5,776,345 A 7/1998 Truitt et al.
5,791,880 A 8/1998 Wilson
5,821,399 A 10/1998 Zeiin
5,869,971 A 2/1999 Sherman
5,947,689 A 9/1999 Schick
5,958,244 A 9/1999 Hartmann
6,063,051 A 5/2000 Stem
6,169,394 B1 1/2001 Frazier et al.
6,173,600 B1 1/2001 Harada et al.
6,217,744 B1 4/2001 Crosby
6,222,371 B1 4/2001 Snyder
6,240,952 B1 6/2001 Schroeder
6,259,242 B1 7/2001 Graham et al.
6,275,717 B1 8/2001 Gross et al.
6,299,769 B1 10/2001 Falkvall et al.
6,309,532 B1 * 10/2001 Tran ..... B01J 47/08 204/267
6,350,382 B1 2/2002 Schick
6,375,847 B1 4/2002 Hartmann
6,404,204 B1 6/2002 Farruggia et al.
6,426,629 B1 7/2002 Edgson et al.
6,439,577 B2 8/2002 Jorgensen et al.
6,502,750 B1 1/2003 Barnes et al.
6,551,841 B1 4/2003 Wilding et al.
6,569,687 B2 5/2003 Doktycz et al.
6,573,734 B2 6/2003 He et al.
6,607,669 B2 8/2003 Schick ..... B01D 61/145 210/103
6,614,212 B2 9/2003 Brugger et al.
6,623,698 B2 9/2003 Kuo
6,650,933 B1 11/2003 Obabkov
6,664,793 B1 12/2003 Sampson et al.
6,673,622 B1 1/2004 Jina
6,683,464 B2 1/2004 Park et al.
6,712,963 B2 3/2004 Schick ..... A61M 1/0209 210/137
6,799,883 B1 10/2004 Urquhart et al.
6,812,709 B2 11/2004 Wieland et al.
6,828,808 B2 12/2004 Srinivasan et al.
6,834,258 B2 12/2004 Schulte et al.
6,930,486 B2 8/2005 Muscarella et al.
7,005,292 B2 2/2006 Wilding et al.
7,287,699 B2 * 10/2007 Liu ..... G01D 3/02 235/375
7,314,453 B2 1/2008 Kuo
7,523,649 B2 4/2009 Corey et al.
7,594,663 B2 9/2009 Jorgensen et al.
7,733,097 B2 6/2010 Schenkl et al.
7,749,445 B2 7/2010 Masters
7,788,047 B2 8/2010 Schick et al.
8,295,921 B2 10/2012 Wang
2002/0043487 A1 4/2002 Schick
2002/0081741 A1 6/2002 Braun, Sr. et al.
2002/0167322 A1 11/2002 He et al.
2003/0020494 A1 1/2003 Desmier et al.
2003/0098690 A1 5/2003 Higo
2003/0145646 A1 8/2003 Henry et al.
2003/0158491 A1 * 8/2003 Krivitski et al. .... A61B 5/6855 600/505
2003/0183249 A1 10/2003 Nissinen et al.
2004/0001906 A1 1/2004 Carhuff et al.
2004/0014233 A1 1/2004 Bannister et al.
2004/0017201 A1 1/2004 Brugger et al.
2004/0155066 A1 8/2004 Schick
2004/0170530 A1 9/2004 Hefti et al.
2005/0109795 A1 5/2005 Furey et al.
2005/0130001 A1 6/2005 Yasumoto et al.
2005/0145020 A1 7/2005 Mathur et al.
2005/0189936 A1 9/2005 Quackenbush et al.
2005/0255491 A1 11/2005 Lee et al.
2006/0014212 A1 1/2006 Benkovic et al.
2006/0042964 A1 3/2006 Mansouri et al.
2006/0086178 A1 4/2006 Discenzo

(56) References Cited

U.S. PATENT DOCUMENTS

| | | | |
|---|---|---|---|
| 2006/0169033 | A1 | 8/2006 | Discenzo |
| 2007/0069720 | A1 | 3/2007 | Goldfine et al. |
| 2007/0149863 | A1 | 6/2007 | Padmanabhan et al. |
| 2007/0237678 | A1 | 10/2007 | Roesicke et al. |
| 2008/0297169 | A1 | 12/2008 | Greenquist et al. |
| 2009/0180513 | A1 | 7/2009 | Schick et al. |
| 2010/0021993 | A1 | 1/2010 | Wang et al. |
| 2010/0158070 | A1 | 1/2010 | Steinboeck et al. |
| 2010/0188111 | A1 | 7/2010 | Fougere |
| 2010/0252490 | A1 | 10/2010 | Fulkerson et al. |
| 2010/0028521 | A1 | 11/2010 | Choi |
| 2010/0286467 | A1 | 11/2010 | Pesach et al. |
| 2011/0153083 | A1 | 6/2011 | Tohidi et al. |
| 2012/0182030 | A1 | 7/2012 | Calciolari et al. |

FOREIGN PATENT DOCUMENTS

| | | | |
|---|---|---|---|
| EP | 1 236 644 | | 9/2002 |
| FR | 2 567 406 | | 1/1986 |
| FR | 2 785 830 | | 5/2000 |
| JP | 59160746 | A | 9/1984 |
| JP | 10-198354 | | 1/1998 |
| JP | 2000-186771 | | 7/2000 |
| JP | 2002-048776 | | 2/2002 |
| RU | 2327977 | C2 | 7/2007 |
| SU | 1671267 | A1 | 8/1991 |
| SU | 1677664 | A1 | 9/1991 |
| WO | WO 92/17775 | | 10/1992 |
| WO | WO 99/02245 | | 1/1999 |
| WO | WO 00/06761 | | 2/2000 |
| WO | WO 0175438 | A2 | 10/2001 |
| WO | WO 03/033120 | | 4/2003 |
| WO | WO 03/106266 | | 12/2003 |

OTHER PUBLICATIONS

"Siemens (unit)", Wikipedia, http://en.wikipedia.org/wiki/Siemens_(unit), Oct. 5, 2009, USA.

Technical Bulletin: "MidGee Cross Flow Filters," A/G Technology Corp., 1996.

Operating Instructions: "MiniKros Sampler System," Spectrum Microgon Inc., 1995.

Technical Bulletin: "MiniKros Sampler System," Spectrum Microgon Inc., May 1995.

Technical Bulletin: "Microgon Techniques for Processing Uniform Latex Particles," Microgon Inc., 1992.

William F. Blatt, Lita Nelsen, Eliseo M. Zipiliyan, and Mark C. Porter, "Rapid Salt Exchange by Coupled Utrafiltration and Dialysis in Anisotropic Hollow Fibers," Separation Science, 7(3) pp. 271-284, 1972.

William F. Bowers and Rudy H. Haschmeyer, "A Versatile Small-Volume Ultrafiltration Cell—Analytical Biochemistry," 25, pp. 549-556, 1968.

UltraTec Filtration System, "Operations Manual Version: 1:28," Scilog, Inc., Apr. 1997.

W.F. Blatt, S.M. Robinson, and Harris J. Bixler, Membrane Ultrafiltration: The Diafiltration Technique and it Microsolute Exchange and Binding Phenomena, Analytical Biochemistry, 26, pp. 151-173, 1968.

Patent Abstract of Japan, Japan Organo Co. Ltd., Publication Date Mar. 14, 1995, Publication No. 07068257.

Patent Abstract of Japan, Asahi Chem Ind. Co., Ltd., Publication Date Mar. 24, 1998, Publication No. 10076143.

Si-Hassen, et al., "Optimisation of an intermittent cross-flow filtration process of mineral suspensions," Journal of Membrane Science, 118 (1996) 185-198.

Carere, "Study of hydrodynamic parameters in the cross-flow filtration of guar gum pseudoplastic solutions," Journal of Member Science, 174 (2000) 135-145.

Webpage of HyClone at www.hyclone.com, undated.

Webpage of Integrate Solution for Biopharmaceutical Fluid Handling: at www.tc-tech.com, undated.

Filvek, "Volumetric Diposable Liquid Filling System Schematic," Innovative Technology Practical Solutions, Brochure, undated.

International Search Report for Internation Application No. PCT/US2003/18980, with international filing date of Jun. 13, 2003.

PCT/US2006/061565 International Search Report and Written Opinion, dated Jun. 4, 2007.

* cited by examiner

FIG. 13
(AMENDED)
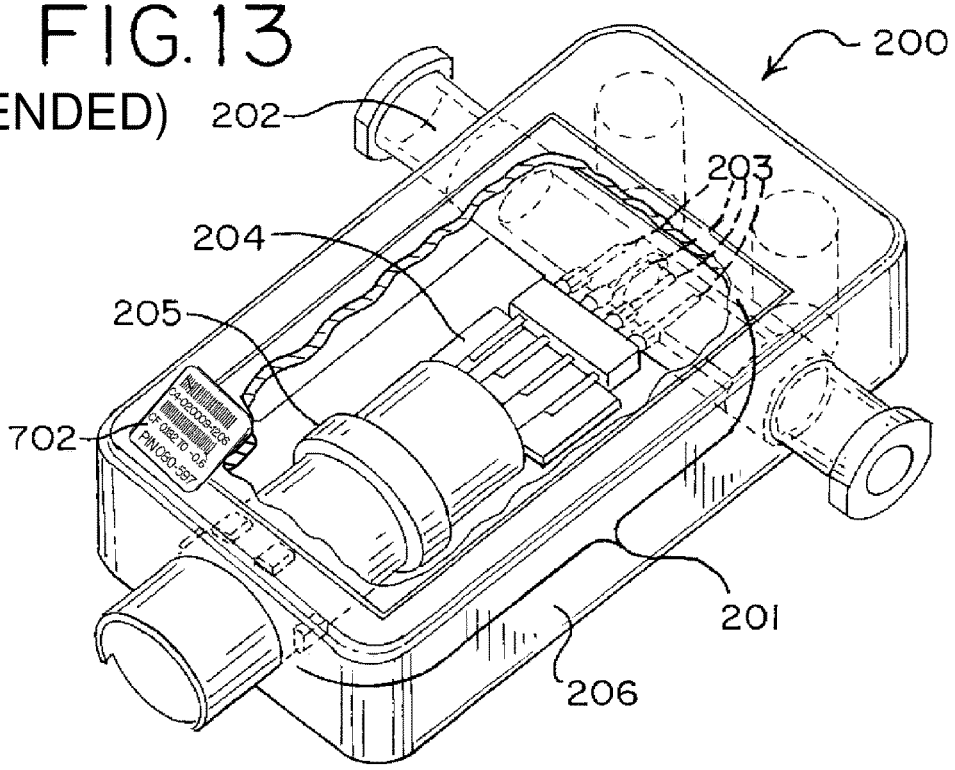

SINGLE-USE MANIFOLDS FOR AUTOMATED, ASEPTIC HANDLING OF SOLUTIONS IN BIOPROCESSING APPLICATIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This *is a Reissue Application of U.S. Pat. No. 9,700,844, filed as application Ser. No. 13/769,971 on Feb. 19, 2013, which* is a continuation of application Ser. No. 11/294,297, filed Dec. 5, 2005, *now U.S. Pat. No. 9,283,521,* which is a continuation-in-part of application Ser. No. 10/764,624, filed Jan. 26, 2004, now U.S. Pat. No. 7,052,603, which is a divisional of application Ser. No. 10/172,082 filed Jun. 14, 2002, now U.S. Pat. No. 6,712,963, each incorporated hereinto by reference.

FIELD OF THE INVENTION

The invention generally relates to the aseptic transfer of solutions out of one or more biological fluid and/or process fluid storage or supply containers. Single-use manifold systems carry out transfers needed in bioprocessing applications. With the invention, automated dispensing is accomplished, preferably in association with one or more disposable conductivity sensors and often with one or more remotely controlled pinch valves.

BACKGROUND OF THE INVENTION

Good manufacturing practices and governmental regulations are at the core of any pharmaceutical, biotechnology and bio-medical manufacturing process or procedure. Such manufacturing processes and procedures as well as associated equipment must undergo mandated, often lengthy and costly validation procedures. Similar issues exist for sensors when needed in such systems, such as conductivity sensors.

For example, the equipment used for the separation and purification of biomedical products must, for obvious reasons, meet stringent cleanliness requirements. The cleaning validation of new or re-commissioned purification equipment (including sensor equipment such as equipment for preparative chromatography or tangential flow filtration) may require as many as 50 test-swabs of exposed surfaces and subsequent biological assays of such test-swabs. For a single piece of purification equipment, the associated and reoccurring cost of a single cleaning validation may readily exceed multiple thousands of dollars.

To reduce such cleaning validation costs and expenses, and/or to reduce the occasions when cleaning is needed or required, the pharmaceutical and biotech industries are increasingly employing, pre-sterilized, single-use, plastic tubing and collapsible, plastic bags for solution transfer and storage. Sterilization is accomplished by exposing the complete tube/bag manifold to gamma irradiation, or to an ethylene oxide atmosphere. The pre-sterilized, aseptically packaged tube/bag manifolds are commercially available (currently from TC Tech; HyClone; St Gobain Performance Plastics, for example) and are used for the manual transfer of solutions. Typically, the solution transfer procedure requires a technician to operate a peristaltic pump and to manually open and close tube clamps for diverting the solution from the reservoir to the storage bags. Although this procedure reduces the cleaning efforts and cleaning validation expense, operator interaction and time still are required, and these approaches are dependent upon operator expertise for consistent accuracy and precision.

Dispensing approaches having automated features (which can include sensors, monitors and programmable controllers) are generally known. Keys et al. U.S. Pat. No. 5,480,063 and U.S. Pat. No. 5,680,960 describe fluid dispensing units which control fluid volumes in conjunction with a closed loop approach, which these patents suggest can avoid the need for venting. The fluid to be dispensed exits the closed loop apparatus through a fill tube, as directed by a controller. Such approaches do not address the cleaning needs and/or cleaning validation costs and expenses, were these types of systems to be used in pharmaceutical and biotech industries for dispensing, directing, combining or separating biological or chemical fluids.

Prior systems can incorporate diaphragm valves, which come into direct contact with the process solution, and these valves are a potential source of contamination. Thus diaphragm valves require costly cleaning validation procedures. In addition, such systems typically lack suitable sensors, especially conductivity sensors.

It has been found that, by proceeding in accordance with the present invention, significant cost savings and better performance can be realized in a system which incorporates automated, aseptic manifolds and sensors within the field of technology which embraces pre-sterilized, single-use plastic tubing and containers having at least one collapsible portion. The components and sensors which contact the biological or chemical fluid are each presterilized and disposable after use.

SUMMARY OF THE INVENTION

The present invention is directed to manifold units which include at least one sensor and which are presterilized and disposable, making them single-use units which are sterilized and packaged so as to be usable "off the shelf" and which thus directly address the problem of tedious and time consuming cleaning and testing at the use site. Multiple embodiments are disclosed. Each includes tubing lengths, at least one sensor and a plurality of single-use storage or collection bags, each having multiple inlet and/or outlet passages which are selectively openable and closeable. The tubing lengths can interact with one or more pinch valves which are operable remotely. Remote operation is automated by a controller programmed to carry out procedures according to a selected embodiment.

It is a general aspect or object of the present invention to provide improved single-use manifolds with at least one sensor for automated, aseptic transfer of solutions in bioprocessing or chemical processing applications.

Another aspect or object of the present invention is to provide improved apparatus and method which combine pinch valve use with disposable, sterilized manifold dispenser units that incorporate at least one disposable sensor.

Another aspect or object of this invention is to provide improved apparatus and method which greatly reduce the expenditure of time and resources devoted to cleaning procedures for transfer equipment used in pharmaceutical and biological industries and laboratories where contamination of biological and/or chemical fluids cannot be tolerated.

An aspect or object of the present invention is to reduce the need for validation procedures for equipment used in separation and purification of fluids such as in conjunction with the preparation, separation, sensing and dispensing of bio-medical products.

Another aspect or object of this invention is that it handles cleanliness requirements for procedures including a sensing function, such as fluid dispensing, preparative chromatography and tangential flow filtration while automating operation thereof.

Another aspect or object is to integrate disposable conductivity sensors with the equipment used in the separation and purification of fluids.

Another aspect or object is to provide the ability to connect disposable conductivity sensors with either a system controller or a user interface.

These and other objects, aspects, features, improvements and advantages of the present invention will be clearly understood through a consideration of the following detailed description.

BRIEF DESCRIPTION OF THE DRAWINGS

In the course of this description, reference will be made to the attached drawings, wherein:

FIG. 13 is a cutaway view of a disposable conductivity sensor;

DESCRIPTION OF THE PARTICULAR EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
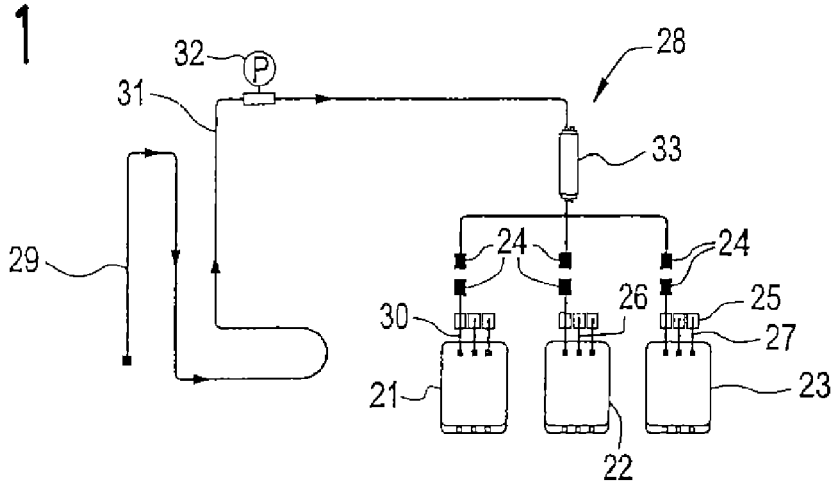
FIG. 1 is a somewhat schematic illustration of a single-use, presterilized system which is especially suitable for solution transfer and collection.
Figure 2:
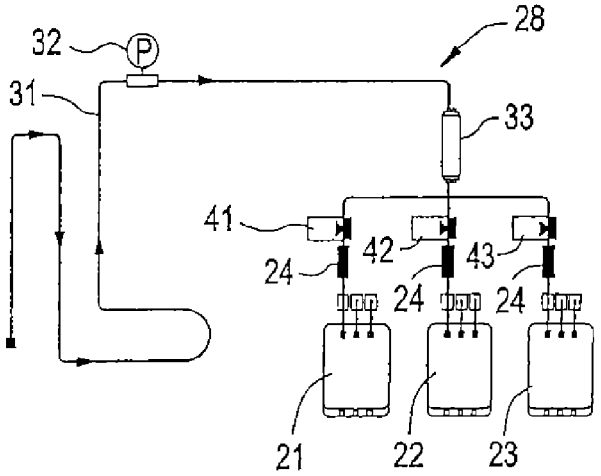
FIG. 2 is an illustration of the single-use system of FIG. 1 in operative association with pinch valves, at least one of which is remotely operable.
Figure 3:
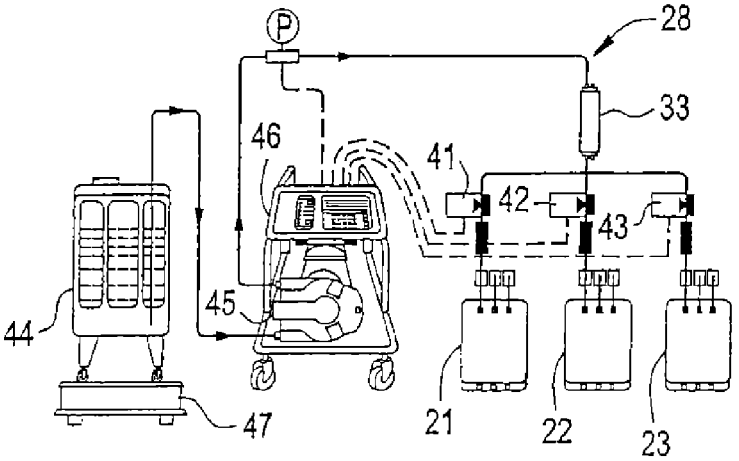
FIG. 3 is an illustration of the combination of the features of FIG. 1 and FIG. 2, shown with means for use to transfer solution through the system; 25

A system particularly designed for use as an automated, aseptic solution transfer system is illustrated in FIGS. 1-3. Fluids processed according to this invention are variously referred to herein as biotechnology fluids, pharmaceutical fluids, chemical fluids, and so forth. These are understood to be solutions, liquids, gas-including systems, and the like. In general, these are referred to herein as biotechnology fluid or fluids.

In the pharmaceutical and biotechnology industries, media preparation departments typically prepare the solutions used in a solution production protocol which follows good manufacturing practices. Media preparation departments are responsible for maintaining solution recipes, preparing and storing buffer solutions and other tasks demanding consistency and accuracy. For example buffer solutions are prepared in large vats, then pumped through a sterilizing filter, such as one having a porosity of 0.1μ. Typically such solutions need to be filled into presterilized, single use storage bags for later use. A media preparation department may also be responsible for providing inoculating solutions to the operators of a bioreactor. At the completion of a bioreactor batch, the reactor broth often is filled into sterile storage bags for later processing.

FIG. 1 shows single-use, presterilized components of the invention. Generally, these disposable components are a manifold and transfer tubing assembly and a plurality of bags. A plurality of single-use storage/collection bags 21, 22, 23 are shown. Each has three tube connections. The primary inlet tubing consists of an aseptic connector 24 and a manual shut-off clamp 25, each of generally known construction. During solution storage, the aseptic connector is covered with an end cap (not shown) to protect the connector 24 from contamination. The manual shut-off clamp 25 is closed during solution storage. These are shown on a first tube connection 30.

The second tube connection 26 consists of a short piece of tubing connected to the bag with a closed manual shut-off clamp. This tubing and clamp arrangement is used to relieve any gas and/or pressure build-up inside the bag during the filling operation. The third tube connection 27 is identical to the second connection and includes a short piece of tubing and a clamp. This can be used as an auxiliary inlet and/or outlet for recirculation of the bag contents.

During a typical bag-filling operation, the first and/or last collection bag can serve the purpose of quality control bags. Often these quality control bags will be smaller in volume, such as one liter. During the initial system priming cycle, the first such quality assurance (QA) bag is filled with process solution. At the end of the dispensing cycle when all of the bags containing the product of the operation, usually larger in volume that the QA bag(s), have been filled, the second QA bag is filled. The solutions contained in the QA bags are subsequently analyzed for contamination or for other quality assurance needs.

When the bag-filling process is completed, the manual shut-off clamps on each bag are closed and the aseptic tube connections are disconnected. During storage, the aseptic connector ends are protected with end caps (not shown).

Turning now to the single-use, sterilized manifold and transfer tubing assembly of FIG. 1, one such unit is generally shown at 28. This represents a generalized manifold for automated solution transfer. An inlet end portion 29 of transfer tubing 31 of the unit 28 is for communication with a container, such as a vat, of solution, typically sterile solution. Sterilized manifold and transfer tubing assembly 28 is shown with an optional, in-line pressure sensor 32 and a single-use sterilizing filter 33. An end portion having serially connected end portions are downstream of the illustrated filter 33. By a suitable movement imparting device or flow imparting unit such a pump 45 (FIG. 3), solution moves from the vat or reservoir through the sensor 32 (if included) and filter 33 and then is serially diverted into the single-use, sterilized storage bags.

FIG. 2 shows a plurality of pinch valves 41, 42, 43 and their respective relative positions with respect to the storage bags. Some or all of the valves can be operated remotely and typically will be pneumatically or electrically activated. A typical set up will have capacity for up to twelve pneumatically actuated pinch valves or more. A like number of storage bags can be accommodated. FIG. 2 shows the relative positions of the pinch valves in association with the optional pressure sensor and the single-use, sterilizing filter. FIG. 3 shows the relative position of the manifold and transfer tubing assembly 28 with the vat 44 and the pump head of a pump unit 45. Preferably, the pump is a high-accuracy, low-shear peristaltic pump which provides gentle and reproducible bag filling. An example is a Watson Marlow 620 RE peristaltic pump head.

Access to the storage bags is provided via the pinch valves. The pinch valves are normally closed, and typical pneumatic pinch valves require pressurized air (for example 80-100 psi) to open. When such a pinch valve is pressurized, solution is allowed to enter the storage bag while the air in the bag escapes through an integral vent filter. The pinch valve(s) are pneumatic or electrically operated pinch valves (currently available from ACRO Associates, Inc). They are installed external to the tubing and are operated by a multi-valve controller (currently available from SciLog Inc.), or another computer-based process logic control (PLC) device. The external pinch valves divert the solution inside the manifold without compromising the sterile environment inside the tubing. Diaphragm valves used in other systems are in constant contact with the process solution, whereas pinch valves do not contact the process solution.

The optional, disposable pressure sensor 32 continuously monitors the filter back pressure. This sensor can provide information to a suitable controller to avoid undesired events. For example, a controller can issue an alarm when a safe, user-defined pressure limit has been exceeded, indicating that the capacity of the sterilizing filter has been exhausted. Details in this regard are found in U.S. Pat. Nos. 5,947,689, 6,350,382 and 6,607,669. These patents and all other references noted herein are incorporated by reference hereinto.

The controller can be a stand-alone unit or be associated with another device. In a preferred arrangement, the controller is associated with the pump unit 45. This is shown at 46 in FIG. 3. Whatever form it takes, the controller controls operation of the remotely operable pinch valve(s). The batch filling rate as well as the batch volume delivered into each storage bag is user-programmable via software residing in the controller. The controller provides automated bag filling by volume, weight or based on filling time and pump rate.

Typically, a user-determined program will be provided for the automated filling of storage bags according to FIGS. 1-3. This is described in terms of a SciPro controller of Scilog, Inc., generally described in U.S. Pat. Nos. 5,947,689, 6,350,382 and 6,607,669. With these approaches, excessive pressure build-up, as well as associated leaks and bag failures are prevented. For example, when so programmed, the controller will stop all pumping action when a user-defined safe pressure limit is exceeded.

An exemplary solution transfer program for controlling the manifold is as follows. In a SciPro edit mode, the user enters and stores a multi-bag metering program. The following is an example of a simple program to fill three, 20-liter storage bags 21, 22, 23.

Filling Program Example

| | | |
|---|---|---|
| 000 | START | The following program steps are entered in an edit mode |
| 001 | CW | Motor Runs Clockwise |
| 002 | RUN | Motor is tuned "ON" |
| 003 | V 100000 | Pinch Valve 41 is Energized, other pinch valves are De-energized |
| 004 | RATE: 5.0 l/min | Pump Rate 5 liters per minute |
| 005 | TIME: 00:04:00 | Pump Runs 4 minutes, Bag 21 is filled with 20 Liters |
| 006 | STOP | Pump "Off", |
| 007 | V 020000 | Pinch Valve 42 is Energized, other valves pinch are De-energized |
| 008 | TIME: 00:00:02 | 2 Second Time delay |
| 009 | RUN | Pump "ON" |
| 010 | RATE: 5.0 l/min | Pump Rate 5 liters per minute |
| 011 | TIME: 00:04:00 | Pump Runs 4 Minutes, Bag 22 is filled with 20 Liters |
| 012 | STOP | Pump "Off" |
| 013 | V 003000 | Pinch Valve 43 is Energized, other pinch valves are De-energized |
| 014 | TIME: 00:00:02 | 2 Second Time Delay |
| 015 | RUN | Pump "ON" |
| 016 | RATE: 5.0 l/min | Pump Rate 5.0 liters per minute |
| 017 | TIME: 00:04:00 | Pump Runs 4 Minutes, Bag 23 is filled with 20 Liters |
| 018 | STOP | Pump "Off" |
| 019 | V 000000 | All Pinch Valves are De-energized |
| 020 | COUNT: 1 | The Program Steps 000 to 020 are executed once |
| 021 | END | |

Changes in the RATE and TIME program steps will accommodate any storage bag volume. Additional "RUN" program blocks can be inserted to increase the number of bags (up to 12 in the example) to be filled. However, an analogous software program can be generated in which storage bags are filled based upon either VOLUME or WEIGHT program commands. A scale with an appropriate capacity is required for bag filling by weight. An optional scale or load cell 47 can be provided to supply data to the controller in this regard. It will be appreciated that this embodiment meters user-defined volumes of fluid, then automatically switches to the next empty storage bag to be filled.

Figure 4:
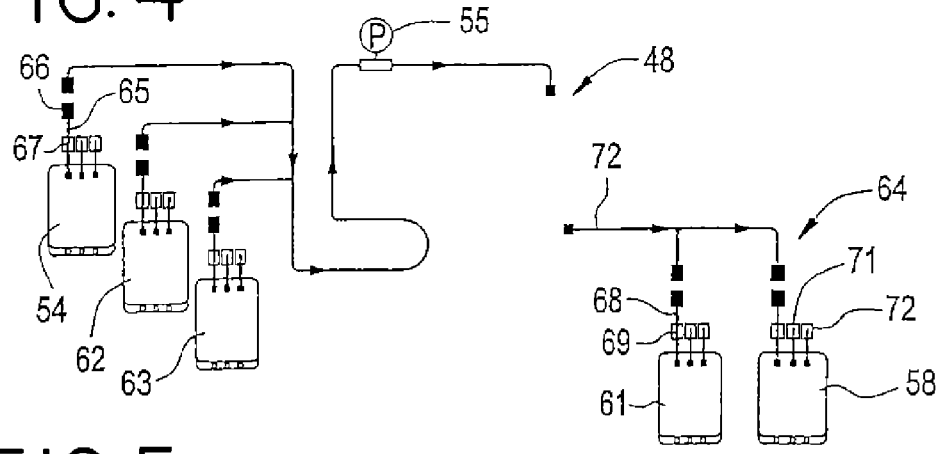
FIG. 4 is a somewhat schematic illustration of a single-use, presterilized system which is especially suitable for use in automated preparative chromatography.
Figure 5:
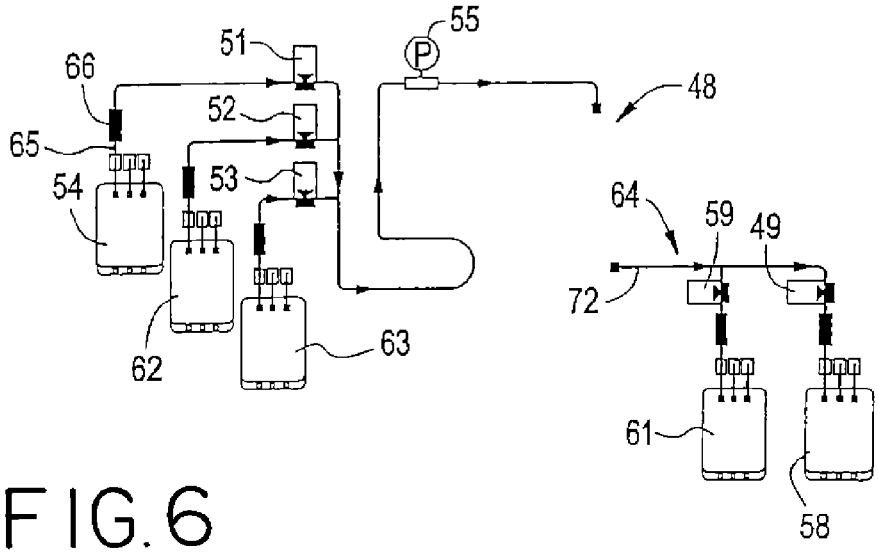
FIG. 5 is an illustration of the single-use system of FIG. 4 in operative association with pinch valves, at least one of which is remotely operable.
Figure 6:
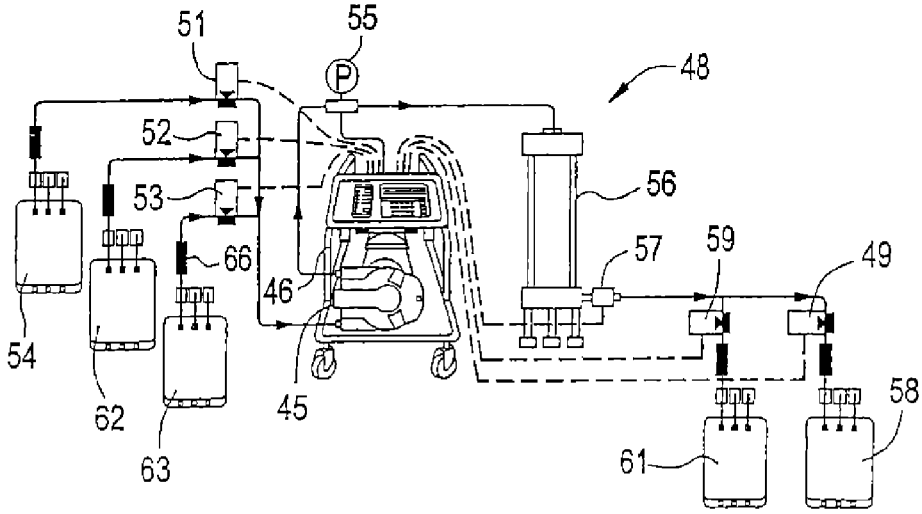
FIG. 6 is an illustration of the combination of features of FIG. 4 and FIG. 5, shown with means for use in transferring solution through the system.

A second embodiment, which is generally illustrated in FIGS. 4-6, achieves automated preparative chromatography. In preparative chromatography, process solution containing the bio-molecule of interest is pumped through a column of gel-like particles (stationary phase) suspended in a liquid. The bio-molecule of interest specifically interacts (via ion-ion interactions, hydrophobic interactions, size exclusion, affinity, for example) with the stationary phase thereby retarding the progress of the bio-molecule through the column. Ideally, other dissolved biomaterials will interact only weakly with the stationary phase and thus will exit the column quickly.

The result is a concentration as well as a separation of the bio-molecule from the rest of the process solution matrix. The introduction of an elution buffer will change the local chemical environment of the stationary phase, thereby causing the bio-molecule to be released and thus able to be collected outside the column in a relatively small volume of elution buffer.

In automated preparative chromatography, the column containing the stationary phase first is washed and/or equilibrated with an appropriate buffer solution. This wash and/or equilibration cycle is followed by a loading cycle during which the process solution is pumped through the column. The bio-molecule of interest adheres to the stationary phase. The loading cycle can take many hours, depending on the process solution volume and pump rate with which the solution is pumped through the column. The loading cycle is followed by a second wash cycle to remove any un-adsorbed biomaterial off the column.

An elution buffer then is introduced to remove the bio-molecule from the column. This removal of the bio-molecule is accomplished either with a step gradient or a linear gradient. After peak collection has been completed, the chromatography column is regenerated and re-equilibrated using appropriate buffer solutions as generally known in the art.

Manifold and transfer tubing assembly 48 represents a generalized manifold for automating preparative chromatography procedures. In operation, and utilizing the controller system, the exemplary pneumatically controlled pinch valve 51 is pressurized and thus opened, thereby providing access to the wash and/or equilibration buffer bag 54. At a user-definable pump rate, the wash buffer is pumped through a disposable, in-line pressure sensor 55, through a bubble trap (not shown), through the chromatography column 56, and through a detector or UV flow cell 57. On exiting the flow cell, the wash/equilibration buffer is collected in a waste container or bag 58 while pinch valve 49 is pressurized and thus open.

During the loading cycle, pinch valves 51 and 49 are opened/pressurized, while the pinch valves 52, 53 and 59 remain closed. The pump unit 45 pumps the process solution through the manifold system 48, the column 56 and the flow cell 57 and is collected in the waste container or bag 58. In some chromatography applications, the process solution exiting the flow cell needs to be stored separately in a "process receiving bag" (not shown) for possible re-processing. Another pinch valve (not shown) would provide access to such a "process receiving bag".

The loading cycle is followed by a wash cycle (valves 51 and 49 are open/pressurized, all other pinch valves are closed) which carries away any un-absorbed material from the column to waste. By opening pinch valves 53 and 49, elution buffer in bag 63 is introduced into the column and is initially pumped to waste. However, when the signal from the UV detector 57 exceeds a user-defined value, pinch valve 59 is opened thereby providing access to a peak collection bag 61 while valve 49 is closed. On the backside of the eluted peak, valve 59 is again closed, while at the same time, valve 49 is opened.

After the material of interest has been collected in bag 61, the chromatographic column 56 requires regeneration and re-equilibration. The column regeneration process is readily automated via access to appropriate buffer solutions (not shown), which are generally as known in the art. Depending on the underlying chromatographic complexity of the application, access to five or six buffer solutions may be required, and these can be provided in their own single-use bags as desired. Similarly, if multiple product peaks are to be collected, additional peak collection bag(s) as well as additional pinch valve(s) may have to be incorporated into manifold and transfer tubing assembly 48.

The single-use, presterilized components of the manifold and transfer tubing assembly 48, shown as a feed section, and of a second tube and bag assembly 64 for chromatographed fluid are shown in FIG. 4. Each of the single storage/collection bags 54, 62, 63 shown in FIG. 4 has three tube connections. The primary inlet tubing 65 consists of an aseptic connector 66 and a manual shut-off clamp 67. During solution storage, the aseptic connector is covered with an end cap to protect the connector from contamination. The manual shut-off clamp is closed during solution storage.

The second tube and bag assembly 64 consists of a short piece of tubing 68 connected to the bag with a closed manual shut-off clamp 69. The second tubing/clamp arrangement 71 is used to relieve any gas and/or pressure build-up inside the bag during the filling operation. The third tube connection 72 is identical to the second tubing/clamp arrangement 71 and is used as an auxiliary inlet/outlet for recirculation of the bag contents.

The single-use storage/collection bags 58 and 61 are connected to the remaining tube manifold 72 as shown in FIG. 4 and FIG. 5. FIG. 5 shows the relative positions of the pinch valves 51, 52, 53, 49 and 59 and the position of the pressure sensor 55. FIG. 6 shows the insertion of the manifold tubing into the peristaltic pump head 45 as well as connections to the chromatography column 56 and the detector 57.

In a typical chromatography application, the single-use storage bags 54 (for wash buffer), 62 (for process solution) and 63 (for elution buffer) have been previously filled, for example by using the embodiment of FIG. 1-3. When the chromatography run is completed, the manual shut-off clamps on each collection bag 58 (for waste), 61 (for peak collection), and for process receiving (when desired, not shown) are closed, and the aseptic tube connections are disconnected. During storage, the aseptic connector ends are protected with end caps.

Referring further to the SciPro controller programmed for controlling the manifold arrangement for chromatography, a mode thereof allows entry and storage of a sequence of simple commands, i.e. RUN, RATE, TIME, VOLUME, P LIMIT 1 and Valve States such as V=000000 (all pinch valves are closed) or V=123456 (all pinch valves are open).

This controller mode is organized in subprogram blocks. The terminating statement of a program block can be a "VOLUME", "TIME", "P LIMIT D1 (or D2)" or "N LIMIT D1 (or D2)" statement. The statement "P LIMIT D1=5%"

reads: "Positive Slope Signal of Detector D1 with a Threshold Value of 5% Full Scale (FS)". See the Chromatography Program Example.

Chromatography Program Example

| | | |
|---|---|---|
| 000 | START | Start of 1st Wash Cycle |
| 001 | CW | Clockwise Motor Direction |
| 002 | RUN | Starts Motor |
| 003 | RATE 0.25 L/M | Pump Rate During Wash Cycle |
| 004 | V 100050 | Wash Buffer 51 Diverted to "Waste" 49 |
| 005 | VOLUME 1.0 Liters | 4 Minutes, End of 1st Wash Cycle, TV = 1.0 L |
| 006 | RATE 1.00 L/M | Loading Rate, Start of Loading Cycle |
| 007 | V 020050 | Process Solution (52) Diverted to "Waste" (49) |
| 008 | TIME: 00:02:00 | 2 Minutes, End of Loading Cycle, TV = 3.0 L |
| 009 | RATE 0.25 L/M | Start of 2nd Wash Cycle |
| 010 | V 100050 | Wash Buffer (51) Diverted to "Waste" (49) |
| 011 | VOLUME 1.0 Liter | 4 Minutes, End of 2nd Wash Cycle TV = 4.0 L |
| 012 | V 003050 | Elution Buffer (53) Diverted to "Waste" (49) |
| 013 | P LIMIT D1 = 5% | Threshold Value Detected Start of Peak Volume Collection |
| 014 | V 003400 | Elution Buffer (53) Diverted to "Collect" (59) |
| 015 | N LIMIT D1 = 10% | D1 Threshold Value, End of Peak Volume Collection |
| 016 | V 003050 | Elution Buffer (53) Diverted to "Waste" (49) |
| 017 | VOLUME 1.0 Liter | Elution Volume, End of Elution, TV = 5.0 L |
| 018 | RATE 0.50 L/M | Start of 3rd Wash Cycle |
| 019 | V 00050 | Wash Buffer (51) Diverted to "Waste" (49) |
| 020 | TIME 00:02:00 | 2 Minutes, End of 3rd Wash Cycle, TV = 6.0 L |
| 021 | STOP | Pump Stops, |
| 022 | V 000000 | All V-valves Closed |
| 023 | END | End of Program |

For example, in line 014, the SciPro switches from "Waste" to "Collect" when the D1 signal has a positive slope and a value greater than 5% FS (line 013). The statement "N LIMIT D1=10%" reads: "Negative Slope Signal of Detector D1 with a Threshold Value of 10% FS". In line 016, the controller switches from "Collect" to "Waste" when the D1 signal has a negative slope (back side of peak) and a value of 10% FS (line 15).

The user can edit and/or modify the values of: RUN, RATE, TIME, VOLUME, P LIMIT 1, N LIMIT D1 and Valve States at any time during a chromatography run. User-designed application programs can be uploaded or downloaded from an external computer at any time by utilizing the computer's hyper terminal.

It will be appreciated that, with this embodiment, sequential scheduling of events are achieved. These include sequential scheduling of wash, load and elution cycles. The controller can initiate buffer selection, loading and peak volume collection. Typical in-line concentration detectors can be Wedgewood UV and/or pH detectors, which have outputs of 4-20 MA outputs which can be monitored simultaneously. A typical pump is a Watson Marlow 620 R peristaltic pump head capable of generating 60 psi at a pump rate of 15 liters per minute.

User-defined detection threshold levels are used for valve switching and peak volume collection. All solution-handling parameters, such as pump rates, column pressure, and valve positions can be monitored and documented in real time and can be printed out or electronically archived.

In a third embodiment, automated tangential flow filtration is carried out using a modified system designed for this use. Previously referenced U.S. Pat. No. 5,947,689, No. 6,350,382 and No. 6,607,669 disclose the automation of tangential flow filtration (TFF) procedures. These are combined with the use of disposable, single-use manifolds, which also include disposable pressure sensors and single-use, collapsible storage bags and the use of remotely operated pinch valve(s).

Figure 7:
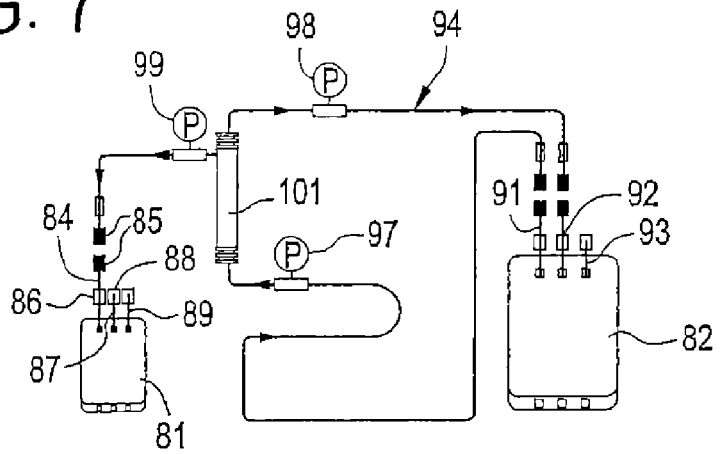
FIG. 7 is a somewhat schematic illustration of a single-use, presterilized system which is especially suitable for automated tangential flow filtration procedures.
Figure 8:
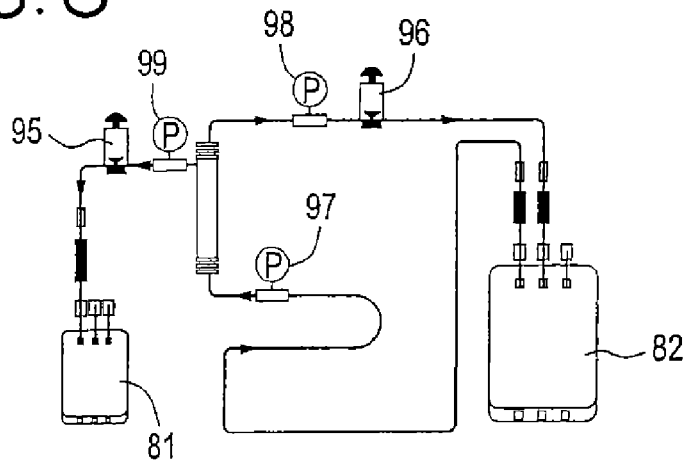
FIG. 8 is an illustration of the single-use system of FIG. 7 in operational association with pinch valves, at least one of which is remotely operable.
Figure 9:
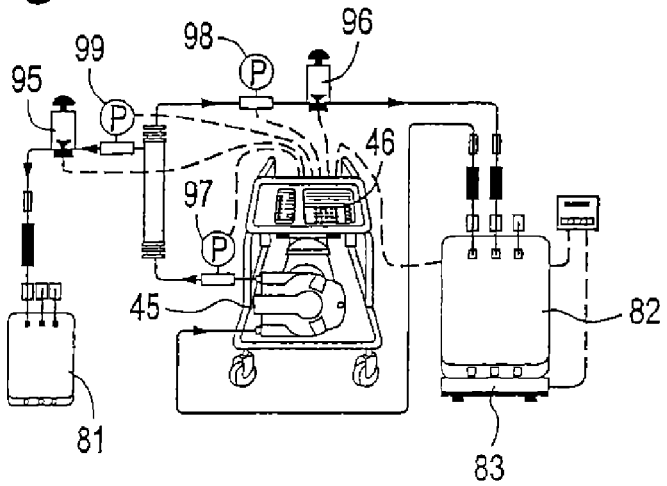
FIG. 9 is an illustration of the combination of the features of FIG. 7 and FIG. 8, shown with means for use to transfer solution through the system.

A typical TFF application that utilizes a single-use, pre-sterilized manifold is shown in FIGS. 7-9. FIG. 7 shows the disposable, pre-sterilized components, including a tubing filtered fluid section having a permeate collection bag 81 as well as a process solution bag 82 within a filtration flow-through section of the tubing. These are aseptically sealed and in a pre-sterilized (for example, irradiated) package. At the beginning of the TFF application, the permeate collection bag 81 is empty and deflated and has been aseptically connected to the TFF manifold. The process solution bag was previously filled, such as by using the system of FIGS. 1-3. The process solution bag 82 is placed onto an optional scale 83 and connected aseptically to the rest of the system. In some applications, weight information can be conveyed to the controller in carrying out the control logic.

The pre-sterilized components of this embodiment are shown in FIG. 7. The permeate collection bag 81 has three tube connections. The primary inlet tubing 84 consists of an aseptic connector 85 and a manual shut-off clamp 86. During solution storage, the aseptic connector is covered with an end cap to protect the connector from contamination. The manual shut-off clamp is closed during solution storage.

The second tube connection consists of a short piece of tubing 87 connected to the bag with a closed manual shut-off clamp 88. The second tubing and clamp arrangement is used to relieve any gas and/or pressure build-up inside the bag during the filling operation. The third tube connection 89 can be identical to the second tubing and clamp arrangement and is used as an auxiliary inlet and outlet for recirculation of bag contents.

Similarly, the process solution bag 82 has three inlet and/or outlet tube connections. The first tube connection 91 is used as an outlet to pump solution out of the bag. The second tube connection 92 serves as a return inlet to accommodate the re-circulated retentate. The third tube connection 93 again serves to relieve any excessive gas and/or pressure build-up inside the bag.

The permeate collection bag and the process solution bag are connected to the filtration tube manifold, generally designated at 94 in FIG. 7. FIG. 8 shows the relative positions of the pinch valves 95 and 96 and the position of three pressure sensors 97, 98, 99. FIG. 9 shows the insertion of the manifold tubing into the head of the peristaltic pump unit 45.

Prior to starting the pump unit 45, all of the manual shut-off clamps are opened except those clamps that relieve any gas and/or pressure build-up inside the bags. Initially the valve 95 is closed and the valve 96 is open, while the pump unit 45 starts to recirculate the solution contained in the process solution bag 82 through a tangential flow filter system 101. The air volume contained in the tubing and tangential flow filter system 101 ends up in the process solution bag 82 where it is vented to the outside through a sterilizing air filter (not shown). Once the optimal pump recirculation rate has stabilized, pinch valve 95 is opened and permeate is collected.

The micro filtration or ultra filtration can be carried out either by constant rate or by constant pressure. Software programs which are suitable to automate the filtration process through the use of the controller 46 are described in U.S. Pat. No. 5,947,689, No. 6,350,382 and No. 6,607,669.

Figure 10:
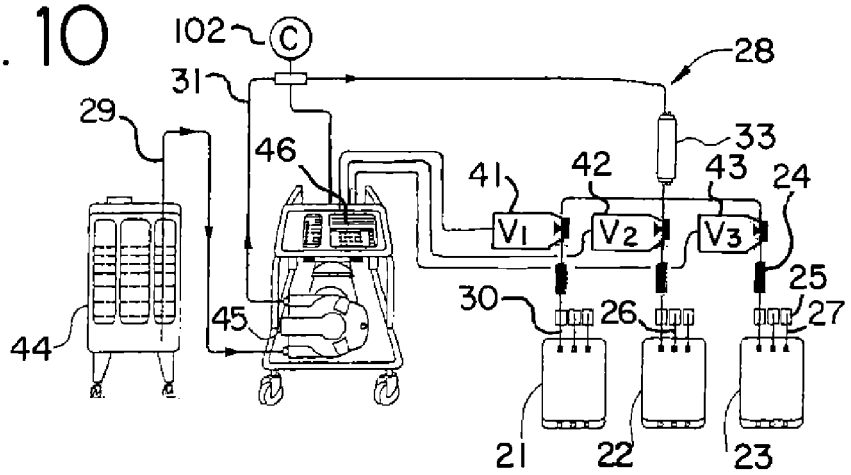
FIG. 10 is an illustration of the single-use system especially suitable for solution transfer and collection in operational association with at least one disposable conductivity sensor.
Figure 11:
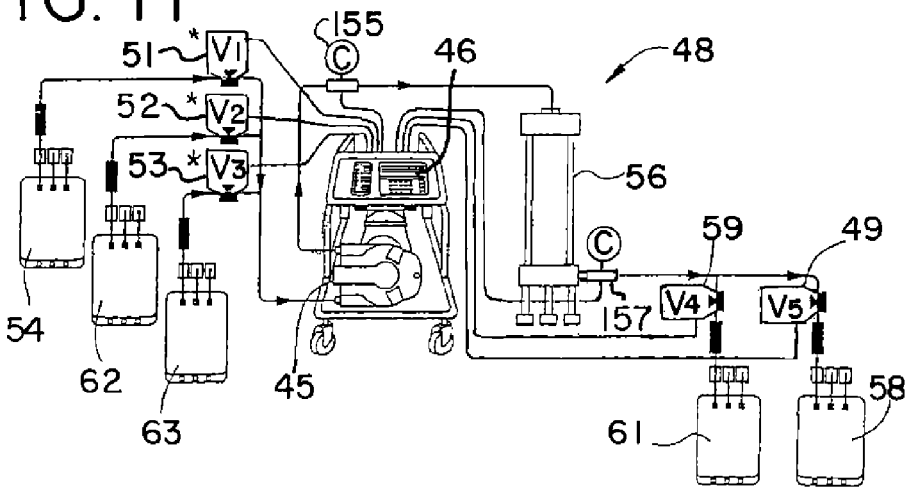
FIG. 11 is an illustration of the single-use system especially suitable for use in automated preparative chromatography in operational association with a disposable conductivity sensor.
Figure 12:
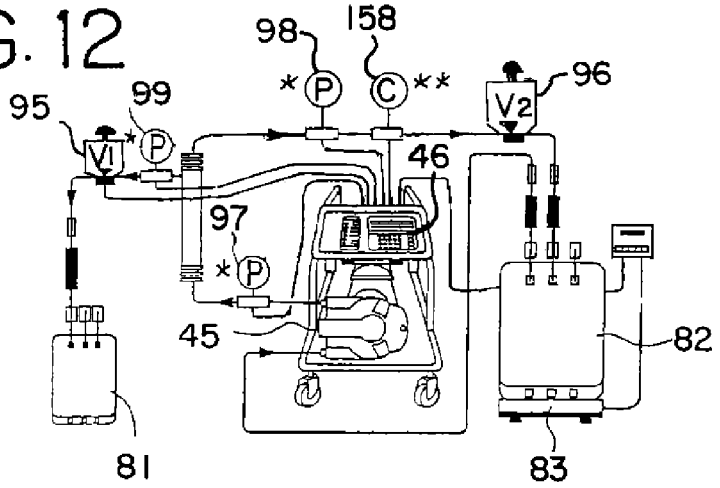
FIG. 12 is an illustration of the single use system especially suitable for automated tangential flow filtration procedures in operational association with at least one disposable conductivity sensor.

The forth, fifth, and sixth embodiments, which are generally illustrated in FIG. 10, FIG. 11, and FIG. 12, respectively, are similar in many respects to the first three embodiments illustrated in FIGS. 1-9. However, the systems shown FIGS. 10-12 include at least one conductivity sensor. Any available conductivity sensor may be used with these systems, for example, toroidal sensors. The conductivity sensor is a pre-sterilized, single-use, disposable, in-line sensor. The embodiment shown in FIG. 13 is a sensor with electrodes.

FIG. 10 shows an aseptic solution transfer system similar to the system of FIGS. 1-3 and like numbers designate like components. However, in this embodiment the in-line pressure sensor 32 is replaced with a disposable in-line conductivity sensor 102. During operation, the solution moves from the vat or reservoir 44 through the sensor 102, the filter 33, and then is serially diverted into the single use storage bags, 21, 22 and 23. The pinch valves 41, 42, and 43, as described above, may be included as desired and may be operated remotely to close the lines into each storage bag and typically will be pneumatically or electrically activated.

The conductivity sensor monitors the conductivity levels of the solution. The levels are reported back either to a user interface, which displays the information, or to the manifold controller 46. Based on the information provided by the conductivity sensor or sensors, the manifold controller 46 (or the user interface in some embodiments) may then modify the operation of a flow imparting unit such as the pump unit 45, open and close the various pinch valves, start user-determined programs, or stop user-determined programs.

The fifth embodiment is generally illustrated in FIG. 11 and is utilized to achieve automated preparative chromatography. As stated above, in preparative chromatography, a process solution containing the bio-molecule of interest is pumped through a column of gel like particles (stationary phase) suspended in a liquid. The bio-molecule of interest interacts with the stationary phase while the other bio-molecules in the process solution will quickly exit the column. The manifold and transfer tubing assembly 48 represents the generalized manifold system as shown in FIGS. 4-6. Unlike the system shown in FIGS. 4-6, the fifth embodiment replaces the in-line pressure sensor 55, the detector 57, or both with an in-line conductivity sensor 155, 157.

The conductivity sensors monitor the conductivity levels of the solution entering the chromatography column 56 and the conductivity levels as the solution leaves the column. The levels are reported back either to a user interface, which displays the information, or to the manifold controller 46. Based on the information provided by the conductivity sensors, the manifold controller 46 (or the user interface in some embodiments) may then modify the operation of the pump unit 45, open and close the various pinch valves, start user-determined programs, or stop user-determined programs.

Figure 14:
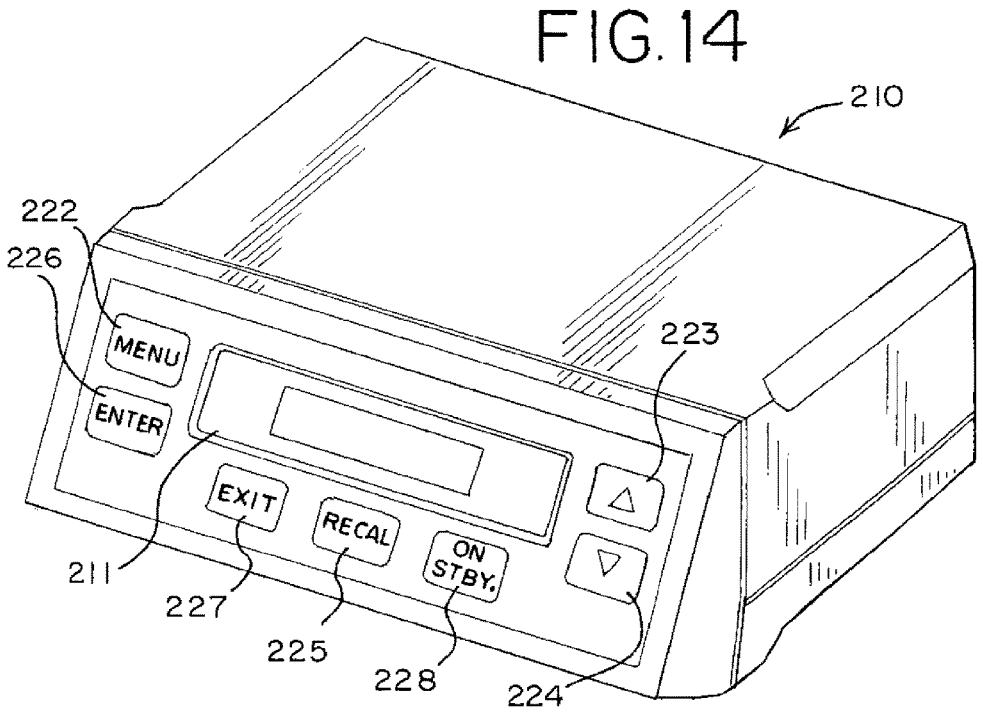
FIG. 14 is shows the exterior of a user interface.

The sixth embodiment, shown in FIG. 12, demonstrates how *electrical* conductivity sensors, *such as the example sensor assembly module shown in FIG. 13 and the user interface or controller as shown in FIG. 14,* may be used in conjunction with a system designed to perform automated tangential flow filtration. The sixth embodiment has the same overall configuration as the system shown in FIGS. 7-9, with the addition of an in-line *electrical* conductivity sensor *assembly module* 158 which is positioned after the pressure sensor 98 and before the pinch valve 96. The automated tangential flow filtration can be carried out with a substantially constant selected rate, a substantially constant selected flow rate, a constant rate or a constant pressure.

The conductivity sensors monitor the conductivity levels of the fluid passing to the process solution bag 82. The conductivity levels are reported back either to a user interface, which displays the information, or to the manifold controller 46. Based on the information provided by the conductivity sensors, the manifold controller 46 (or the user interface in some embodiments) may then modify the operation of a flow imparting unit such as the pump unit 45, open and close the various pinch valves, start user-determined programs, or stop user-determined programs. The conductivity sensor 158 is useful in TFF as it monitors the concentration or absence of molecules passing through the tubing to the process solution bag 82. For example, if, the conductivity sensor measures abnormally high conductivity levels during the cleaning or operation of the tangential flow filter, it may signal to the controller or user that the filter is defective. On the other hand, if the conductivity sensor measures abnormally low conductivity levels during the cleaning or operation of the tangential flow filter, it may signal that the filter or tubing is clogged.

The preferred embodiment of an in-line conductivity sensor has two components: the user interface or the controller 46 and the disposable sensor assembly module. Further description of the in-line, single-use or disposable conductivity sensor is found in U.S. Pat. Nos. 7,788,047, 7,857,506 and 7,927,010 and in U.S. Patent Application Publication No. 2009/0180513, entitled "Disposable, Pre-Calibrated, Pre-Validated Sensors for use in Bio-processing Applications," incorporated hereinto by reference. However, in other embodiments, the functionality of each component may be combined with or moved to the other component.

The disposable sensor assembly module, generally designated as 200 in FIG. 13, contains inexpensive components. Typically, the *electrical conductivity* sensor assembly module contains a short tubular fluid conduit 202 and a sensing portion, generally designated as 201, which includes electrodes 203, a printed circuit board (PCB) 204 and a sensor-embedded non-volatile memory chip (not-shown). In this embodiment, four electrode pins 203 are press-fitted through four linearly arranged holes in the fluid conduit wall 202, and are placed in the pathway of fluid progressing through the system that is connected at both ends of the fluid conduit 202. The electrodes 203 and holes are epoxied, connected or sealed into place to prevent leaks or contamination. The PCB [104] *204* is enclosed in a sheath 205. To prevent contamination and to make the assembly 201 impervious to any liquid, the combination of the sheath 205, PCB 204, electrodes 203 and to some extent the fluid conduit 202 is sealed in an exterior housing 206. *It will be appreciated that, as shown in FIG. 13, an etched or printed label 702, containing one or more barcodes and/or other printed indicia, is affixed to the exterior housing of the electrical conductivity sensor assembly module. The barcodes and/or other printed indicia encode some or all of the information contained in the electrical conductivity sensor and/or electrical conductivity sensor assembly module.*

Toroidal *electrical* conductivity sensors may be used in place of the electrodes in the *electrical conductivity* sensor assembly [202] *module 200*. The toroids of the toroidal sensors may be arranged in a non-obtrusive manner around the fluid circuit. Typically, two toroids are used. One toroid is used to "drive" or induce a current through the fluid, while the other "senses" or measures the induced current through the fluid.

The electrodes or toroids are connected to the PCB 204. The PCB may contain various components, such as a thermistor to measure the temperature of the fluid in the fluid circuit 202 or a non-volatile memory chip or EEPROM. The PCB is connected to a user interface, control unit, or controller 46. The controller 46 or user interface connects to and accesses the PCB 204, its components, and the electrodes 203 by a plug-in wires or leads (not shown).

The controller 46 or the user interface produces the current that drives the electrodes or toroids and measures the conductivity by measuring the current on the "sensing" electrodes or toroids. The conductivity of the fluid passing through the fluid conduit is measured by driving a current through one or more electrodes, and then using the remaining electrodes to measure the current that passes through the fluid. The current or the voltage drop measured is proportional to the conductivity of the fluid passing through the fluid conduit.

The user interface or controller 46 may access calibration information stored in the non-volatile memory of the sensor. During production of the disposable sensors 200, small variations in the design and placement of the electrodes 203 as well as variations in the accuracy of the thermistors may lead to inaccurate conductivity measurements. However, each sensor is individually calibrated to account for the adverse effects due to these small variations. The sensor specific calibration information is stored in the non-volatile memory of the sensor.

This calibration information may include a temperature offset and a conductivity constant. The temperature offset represents the linear difference between the known temperature of the fluid and the temperature measure by the sensor at the time of calibration. The conductivity constant represents the difference between the known conductivity of the fluid and the conductivity measure by the sensor at the time of calibration. When measuring the conductivity of the fluid in the fluid conduit, the user interface or controller 46 will retrieve the calibration information to use in the calculations for conductivity. The temperature offset and conductivity constant are later utilized by the user interface or controller 46 to calculate the actual conductivity of the biotechnology fluid passing through the fluid conduit 202.

The calibration information may also include information about the method of calibration, the statistical variance among different sensors in the same lot, and the date when the sensor was last calibrated.

In addition to the calibration information, production information may be stored in the non-volatile memory on the sensor. Production information may include items such as the date, time, or lot number for when the sensor was manufactured.

FIG. 14 shows a possible embodiment of a user interface, as generally designated 210. As stated above, the sensor 200 may be connected to either the controller 46 or a user interface 210. While both the user interface 210 and the controller 46 may provide the same functions and display similar information, the embodiment of user interface 210 in FIG. 14 may be advantageous. The user interface 210 is somewhat more portable in comparison to an entire manifold system or controller 46, may be utilized separately from the entire system, and allows for either the user interface or components of the system to be independently upgraded or replaced. Other embodiments might replace the controller 46, with the user interface 210. In these embodiments, the smaller user interface 210 also has control logic to receive data from the system and to operate the various valves and pumps. In keeping with the invention, the terms user interface and controller may be used interchangeably.

The user interface 210 has a display 211 and several input keys on its face. These keys include the Menu key 222, the Up key 223, the Down key 224, the Re-Cal key 225, the Enter key 226, the Exit key 227 and the Sensor On/Sensor Standby key 228. To turn the user interface on, the user must press the Sensor On key 228. During normal operation, the display 211 typically reports the conductivity of the fluid being measured by the system in Siemens, the temperature of the fluid in degrees Centigrade, the percent of total conductivity, and a graphical representation of the percent of total conductivity.

Figure 15:
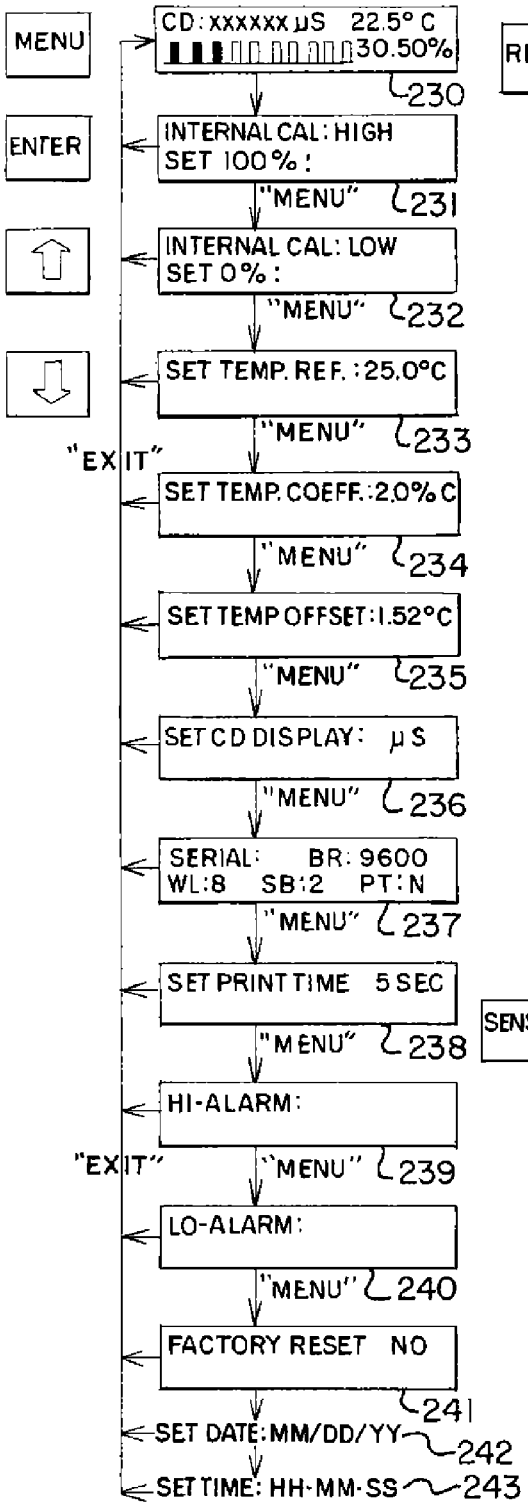
FIG. 15 is an exemplarily flowchart of the different screens presented by the user interface.

The Menu key 222 allows users to progress through different menus as shown in FIG. 15. The display screen 221 initially presents "RUN" screen 230, which typically displays the conductivity of the fluid being measured by the system in Siemens, the temperature of the fluid in degrees Centigrade, the percent of total conductivity, and a graphical representation of the percent of total conductivity. If the user repeatedly presses the Menu key 222, the screen 221 will display the High Conductivity Value 231 (for example 80,000 μS) and then the Low Conductivity Value 232 (for example 0 μS). If the user continues to press the Menu Key 222, the user interface 220 will display the calibration information retrieved from the non-volatile memory of the sensor.

The user interface does not necessarily have to use the calibration information stored on the sensor. In the illustrated embodiment, the user may modify the calibration information utilized by the user interface 220 without permanently modifying the information stored in the non-volatile memory on the sensor. The user may manually change the calibration information utilized by the user interface 220 by selecting the Up or Down arrow keys 223, 224 when presented with the corresponding screen.

The modifiable calibration information may include the Reference Temperature 233, the Temperature Coefficient 234, and the Temperature Offset 235. By pressing the Menu Key 222, the user may modify by using the Up or Down arrow keys 223, 224 the units in which conductivity is displayed 236, the setting for the serial port 237, the different print times for the print option 238, the maximum conductivity measurement at which point the user interface 220 produces a high audible alarm 239 or low audible alarm 240. The user may also select to restore or re-install the factory calibration values 241, or change the date 242 and time 243. When presented with any of the above mentioned options, the user may return the user interface to normal operations without changing the option by pressing the Exit Key 227.

Figure 16:
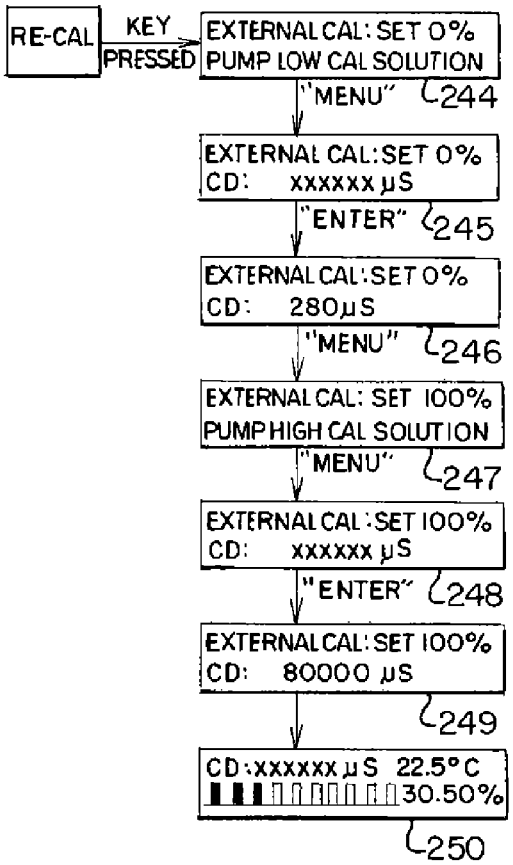
FIG. 16 is an exemplarily flowchart of the different screens presented by the user interface when the user selects to run the recalibration program.

The user may also re-calibrate the sensor or overwrite the calibration information stored in the non-volatile memory chip by selecting the Re-cal key 225, which runs the recalibration program. As shown in FIG. 16, the recalibration program displays the calibration information on the display screen 221. The user can scan through the calibration information by using the Up and Down arrow keys 223, 224. By pressing the Menu key 222, the user may select a specific piece of calibration information, such as the Pump Low Calculation solution 244, External Calibration Data 245 and 246, and the High Pump Calibration 247, 248, and 249. The user may then modify the value for each piece of calibration information by selecting the Up or Down keys 223, 224.

After the information is modified, the new value overwrites the stored information in the non-volatile memory of the sensor when the user presses the Enter Key 225. The display 211 will then report the current readings 250 as computed using the new calibration information. In the future, when the user selects "Factory Reset" 241, the current settings of the user interface are replaced with those values entered by the user during the last recalibration program. However, if the user wants to end the recalibration program without changing the options, he or she need only press the Exit key 227.

Figure 17:
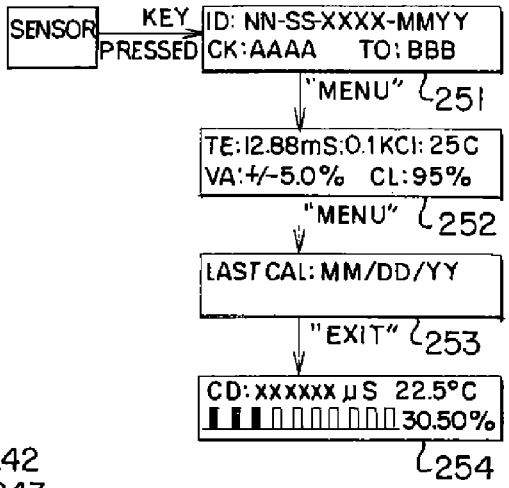
FIG. 17 is an exemplarily flowchart of the different screens presented by the user interface when the user selects to view the calibration and production information.

The user interface 220 may also include a sensor key (not shown). As shown in FIG. 17, when the user presses the Sensor key, the user interface retrieves the production information and calibration information stored in the non-volatile memory of the sensor. The calibration information may include information that was replaced by the recalibration program. Initially, this operation displays the unique ID number for the sensor 251. By pressing the Menu key 222, the user may view other calibration information 252, such as the type of solution used during calibration as shown, the temperature of the calibration solution, and the statistical information for the sensor. The user may also view the date when the sensor was last calibrated or recalibrated 253. The user may return the user interface to normal operations 254 by pressing the Exit Key 227.

FIG. 13 shows the top view or the component view of the sensor 200. The electrodes 203 are connected to the underside of the PCB 204. A surface-mounted thermistor is in thermal contact with two of the conductivity electrode pins when four are provided. A second, important function of the thermistor is to act as a pull-up resistor for the non-volatile memory chip, thereby assuring proper functioning of the memory device. The thermistor is used to monitor the temperature of the solution in the fluid conduit 202, via thermal conductance, such being transmitted to the user interface 210. The user interface 210 reports the solution temperature data and utilizes the temperature data to correct or normalize the solution conductivity reading.

A sensor-embedded non-volatile memory chip or an EEPROM is mounted on the surface of the PCB 204. The non-volatile memory chip or EEPROM is used to store sensor-specific information. This information can be called up, displayed and printed out, on demand, by the user interface 210.

The sensor-specific information is electronically entered into the non-volatile memory chip during factory calibration of the conductivity sensor 200. The sensor-specific information may include the following: Cell Constant (K), Temperature Offset, the unique Device ID, and the Calibration Date, the production lot number of the sensor, the production date of the sensor, the type of fluid used for calibration, the actual temperature of the fluid used, and "out-of-box" sensor performance value.

During production, small differentiations in the electrodes 203, the respective angles of the electrodes, and the gaps between the individual electrodes will result in different conductivity readings for each sensor produced. These differences can significantly affect accuracy. In keeping with the invention, these differences are successfully addressed by having each sensor normalized or calibrated as a part of its manufacturing procedure.

In the illustrated example, each *electrical* conductivity sensor [108] *assembly module 200* is calibrated using certified 0.100 molar KCl (potassium chloride) solution maintained at 25.0° C. The conductance, which is dependent on the cell geometry and the solution resistivity, is determined by measuring the voltage drop across the electrodes. The measured conductance together with known solution *electrical* conductivity allows the calculation of the sensor-specific Cell Constant (K). The Cell Constant (K) is determined by the following equation:

$$[\text{Solution Conductivity, (S/cm)}]/[\text{Conductance(S)}]=[\text{Cell Constant, K, (cm}^{-1})]$$

The sensor-specific Cell Constant (K) is then stored in the non-volatile memory of the conductivity sensor 200.

For example, the solution conductivity for a 0.100 molar KCl solution is known to be 12,850 μS (or 0.01285 S) at 25.0° C. The typical measured conductance for a 0.100 molar KCl solution using a sensor with a ⅛ inch Luer conductivity cell with a 0.10 inch electrode separation is 0.0379 Siemens. Using the equation above, the corresponding Cell Constant (K) for the particular disposable sensor of this illustration is calculated to be 0.339 $cm^{-1}$.

Once the Cell Constant (K) is calculated it is stored on the sensor. The user interface will recall the Cell Constant (K) from the sensor. When undergoing normal operations, the user interface 210 measures the conductance in Siemens of the solution flowing through the fluid conduit 202 by passing a current through the electrodes 203 and measuring the current across the two inner electrodes 203. The user interface 210 will then use the Cell Constant (K) for this particular disposable sensor to determine the electrical conductivity of the solution flowing through the fluid conduit. The user interface calculates the solution's electrical conductivity by multiplying the measured conductance by the Cell Constant (K), as demonstrated in the following equation:

$$[\text{Cell Constant, K, (cm}^{-1})]\times[\text{Conductance (S)}]=[\text{Solution Conductivity, (S/cm)}]$$

The sensor, once calibrated, provides a linear response for NIST traceable standard solutions ranging from 1 to 200,000 μS.

The temperature of a solution will also affect its electrical conductivity. As a result, the sensor must also measure and account for the temperature of the solution to achieve an accurate electrical conductivity measurement. Ordinarily, un-calibrated thermistors will have a variance of ±5% between their measured reading and the actual temperature. A calibrated thermistor may achieve a variance of ±1% or less.

In this regard, a sensor-specific Temperature Offset is calibrated at the factory. To determine the Temperature Offset, temperature readings are made while a 25.0° C. KCl solution is pumped through the fluid conduit and over the electrodes. A comparison is then made between the temperature reading of the un-calibrated thermistor on the sensor (Tsen) with that of a NIST-traceable thermometer or thermistor (Tref). The difference between the two readings is the Temperature Offset (Tref-Tsen=TempOffset). The Temperature Offset may have either a positive or a negative value. The sensor-specific Temperature Offset is then stored in the non-volatile memory on the sensor.

Each sensor has an "out-of-box" performance variance value which is also stored on the sensor, typically in the non-volatile memory chip. This "out-of-box" value is a statistically derived performance variance (measured in 0.100 molar KCl at 25.0° C.) that represents the maximum measurement error for that specific sensor within a 98% confidence limit. The statistically derived variance value is based on the performance analysis of all calibrated sensors within a production run, typically of between about 100 and about 500 sensor assemblies. The factory determined performance variance represents a predictive, "out-of-box" sensor performance level. This statistical treatment is analogous to and representative of a sensor validation procedure. Factory pre-validated conductivity sensors are thereby provided. The meaning of "pre-validated" is further illustrated herein, including as follows.

In the preferred embodiment, each conductivity sensor undergoes two factory measurements. The first measurement involves sensor calibration and determination of the specific Cell Constant (i.e. response factor) using a 0.100 molar KCl solution at 25.0° C. as described herein. In another separate and distinct measurement with 0.100 molar KCl solution at 25.0° C., the solution conductivity is experimentally determined using the pre-calibrated sensor. When taking into account the experimentally derived solution conductivities for all pre-calibrated sensors, the mean conductivity value closely centers around the theoretical value of 12,850 μS with a 3-sigma standard deviation of +/−190 μS or +/−1.5% An operator may access this information via the user interface 210 or Conductivity Monitor.

In addition to the calibration information, such as the Cell Constant (K) and the Temperature Offset, the sensor-specific Device ID, Calibration Date, and statistical information are stored in the non-volatile memory. The Device ID is stored as a string of numbers, for example: nn-ss-xxxx-mmyy. In this example, the variables represent the sensor lot number (nn), fluid conduit size (ss), the device serial number (xxxx) and the manufacturing date by month and year (mmyy). For example, sensor containing the Device ID of 02-02-0122-1105 means that this sensor was the 122$^{nd}$ sensor made in lot 02 of conduit size 02 (a fluid conduit with a diameter of ⅜" or 9.5 mm having a barb connector), manufactured in November of 2005. In this illustration, the sensor-specific Calibration Date or the date on which the sensor was calibrated using 0.100 molar KCl solution at 25.0° C. is also stored in the sensor's non-volatile memory as a separate data entry.

Additionally, statistical information or statistical data about the entire lot may also be stored in the non-volatile memory. For example, the average cell constant for lot 122 may be stored in the non-volatile memory of each sensor in lot 122. The standard deviation for cell constants for each lot may also be stored (i.e. "out-of-box" variance value) in the non-volatile memory of each sensor produced in that lot. This allows the user to determine whether a particular sensor is within the statistical range to achieve the proper margin of error for a specific experiment or bio-processing operation. As those skilled in the art will appreciate, other known statistical methods may be utilized, the results of which may be stored in the non-volatile memory on the sensing device.

In addition to storing the Cell Constant (K), Temperature Offset, Device ID, the Calibration Date, and other information in the non-volatile memory on the sensor, a summary of this information may be printed on the outside of the sensor. This information may be consulted by the user, used to later re-calibrate the sensor, and allows the user to input the printed information directly into the user interface.

It will be understood that the embodiments of the present invention which have been described are illustrative of some of the applications of the principles of the present invention. Numerous modifications may be made by those skilled in the art without departing from the true spirit and scope of the invention.

The invention claimed is:

1. A manifold system for biotechnology uses, comprising:

a manifold unit which is pre-sterilized and disposable so as to be adapted for single-time usage, including:

(a) at least one length of tubing having at least one inlet end portion, at least one outlet end portion, an outside surface, and an inside surface which is sterilized for passage of a biotechnology fluid therethrough, (b) a plurality of single-use containers, each container having an access port, and (c) at least one aseptic connector that operatively connects said length of tubing with each said single-use container;

a plurality of valves operable to engage said length of tubing, the valves being remotely operable valves;

a disposable filter positioned along said length of tubing such that the biotechnology fluid can flow therethrough at a location upstream of said outlet [and] *end* portion;

at least one pre-sterilized, calibrated and disposable electrical conductivity sensor adapted for single-time usage;

the electrical conductivity sensor senses the electrical conductivity of the biotechnology fluid within the tubing and has a memory component capable of storing data, the memory component including a sensor-specific temperature offset assigned to that specific sensor during calibration of the sensor, wherein said temperature offset was determined during manufacture employing a calibration solution, including determining the actual temperature (Tref) value of the calibration solution, using the specified pre-calibrated sensor to measure the temperature (Tsen) value of the calibration solution, and mathematically combining said Tref and said Tsen into said sensor specific temperature offset;

at least one disposable pressure sensor positioned along said length of tubing such that the biotechnology fluid can flow therethrough at a location selected from the group consisting of upstream, downstream, both upstream and downstream of said disposable filter, and upstream of said outlet end portion; and a controller which controls operation of said remotely operable valves, said controller having control logic which dictates the timing of opening and closing of said remotely operable valves.

2. The system in accordance with claim 1, wherein said control logic of the controller [dictates] *is operable to dictate* the rate of flow of the biotechnology fluid.

3. The system in accordance with claim 2, wherein said control logic of the controller [determines] *is operable to determine* the extent of filling of at least one of the single-use containers by processing data monitored by the system to achieve filling of the single-use container by volume, by weight, or by flow rate and filling time.

4. The system in accordance with claim 1, wherein said control logic of the controller [determines] *is operable to determine* the extent of filling of at least one of the single-use containers by processing data monitored by the system to achieve filling of the single-use container by volume, by weight, or by flow rate and filling time.

5. The system in accordance with claim 1, wherein said control logic is operable to activate flow of the biotechnology fluid and opens one of the remotely operable valves for a length of time needed to flow a selected volume or weight of biotechnology fluid into a single-use container associated with that remotely operable valve, and wherein said control logic is operable to activate flow of the biotechnology fluid and opens another of the remotely operable valves for a length of time needed to flow a selected volume or weight of biotechnology fluid into another [valve] single-use container until a user-selected number of single-use containers are filled.

6. The system in accordance with claim 1, wherein said outlet end portion of the tubing has a plurality of serially arranged outlet passageways each having one of said aseptic connectors for operable connection with one of said single-use containers, and wherein one of said remotely operable valves controls passage of the biotechnology fluid from the tubing to the single-use container [bag].

7. The system in accordance with claim 1, wherein the disposable pressure sensor is positioned along said length of tubing such that the biotechnology fluid can flow therethrough at a location upstream of said outlet end portion.

8. The system in accordance with claim 1, wherein said system is for tangential flow filtration, wherein one said single-use container is a process solution container and another said single-use container is a permeate collection container, wherein said tubing includes at least two sections including a filtration flow-through section and a filtered fluid section, said filtration flow-through section includes said process solution container, said filtered fluid section includes said permeate collection container, and said disposable filter is between said filtration flow-through section and said filtered fluid section, whereby fluid from said process solution container can be filtered through said disposable filter and collected in said permeate collection container.

9. The system in accordance with claim 8, wherein said inlet end portion is within said filtration flow-through section and in operative communication with said process solution single-use container, said filtration flow-through section further includes a recirculation length of tubing having one of said remotely operable valves between an exit port of said disposable filter and said process solution single-use container.

10. The system in accordance with claim 9, wherein the disposable pressure sensor is positioned along said filtration flow-through section tubing such that the biotechnology fluid can flow therethrough at a location downstream of said disposable filter.

11. The system in accordance with claim 8, wherein the disposable pressure sensor is positioned along said filtration flow-through section tubing such that the biotechnology fluid can flow therethrough at a location upstream of said disposable filter.

12. The system in accordance with claim 8, wherein the disposable pressure sensor is positioned along said filtered fluid length of tubing such that the biotechnology fluid can flow therethrough at a location between said disposable filter and said permeate collection single-use container.

13. The system in accordance with claim 1, wherein at least one of the single-use containers includes [a shut-off clamp for its access port, and wherein said single-use container further includes] a port that releases gas or pressure build-up from said container, an auxiliary access port, and a shut-off clamp for [said] *its* access port and for said auxiliary access port.

14. The manifold system in accordance with claim 1, wherein the container is a bag, and the remotely operable valve is a pinch valve that engages the outside surface of the length of tubing.

15. A manifold system for biotechnology uses, comprising:

a manifold unit which is pre-sterilized and disposable so as to be adapted for single-time usage, including:

([d] *a*) at least one length of tubing having at least one inlet end portion, at least one outlet end portion, an outside surface, and an inside surface which is sterilized for passage of a biotechnology fluid therethrough, ([e] *b*) at least one single-use container having an access port, and ([f] *c*) at least one aseptic connector that operatively connects said length of tubing with said at least one single-use container;

a plurality of valves operable to engage said length of tubing, the valves being remotely operable valves;

a disposable filter positioned along said length of tubing such that the biotechnology fluid can flow therethrough at a location upstream of said outlet [and] *end* portion;

at least one pre-sterilized, calibrated and disposable electrical conductivity sensor adapted for single-time usage;

the electrical conductivity sensor senses the electrical conductivity of the biotechnology fluid within the tubing and has a memory component capable of storing data, the memory component including a sensor-specific temperature offset assigned to that specific sensor during calibration of the sensor, wherein said temperature offset was determined during manufacture employing a calibration solution, including determining the actual temperature (Tref) value of the calibration solution, using the specified pre-calibrated sensor to measure the temperature (Tsen) value of the calibration solution, and mathematically combining said Tref and said Tsen into said sensor specific temperature offset;

at least one disposable pressure sensor positioned along said length of tubing such that the biotechnology fluid can flow therethrough at a location selected from the group consisting of upstream, downstream, both upstream and downstream of said disposable filter, and upstream of said outlet end portion; and a controller which controls operation of a plurality of said remotely operable valves, said controller having control logic which [dictates] *is operable to dictate* the timing and the extent of opening and closing of a plurality of said remotely operable valves.

16. The system in accordance with claim 15, wherein said control logic of the controller [dictates] *is operable to dictate* the rate of flow of the biotechnology fluid.

17. The system in accordance with claim 16, wherein said control logic of the controller [determines] *is operable to determine* the extent of filling of the single-use container by processing data monitored by the system to achieve filling of the single-use container by volume, by weight, or by flow rate and filling time.

18. The system in accordance with claim 15, wherein said control logic of the controller [determines] *is operable to determine* the extent of filling of the single-use container by processing data monitored by the system to achieve filling of the single-use container by volume, by weight, or by flow rate and filling time.

19. The system in accordance with claim 15, wherein the disposable pressure sensor is positioned along said length of tubing such that the biotechnology fluid can flow therethrough at a location upstream of said outlet end portion.

20. The system in accordance with claim 15, wherein the disposable pressure sensor is positioned along said length of tubing such that the biotechnology fluid can flow therethrough at a location downstream of said disposable filter and upstream of said outlet end portion.

21. The system in accordance with claim 15, wherein the single-use container includes a shut-off clamp, and wherein said single-use container further includes an access port that releases gas or pressure build-up from said container, and

[said container and] further includes an auxiliary port, further including a shut-off clamp for said auxiliary access port.

22. The [manifold] system in accordance with claim 15, wherein the container is a bag, the remotely operable valve is a remotely operable pinch valve that engages the outside surface of the length of tubing, [the flow imparting unit is a pump,] and the control logic [controls or dictates] *is operable to control or dictate* the timing of opening and closing of the remotely operable pinch valve.

23. A system for biotechnology uses, wherein said system is for tangential flow filtration, comprising: a manifold unit which is pre-sterilized and disposable so as to be adapted for single-time usage, including: (a) at least one length of tubing having at least one inlet end portion, at least one outlet end portion, an outside surface, and an inside surface which is sterilized for passage of a biotechnology fluid therethrough, (b) a plurality of single-use containers, each having an access port, one said single-use container is a process solution container and another said single-use container is a permeate collection container, (c) said tubing includes at least two sections including a filtration flow-through section and a filtered fluid section, said filtration flow-through section includes said process solution container, said filtered fluid section includes said permeate collection container, (d) an aseptic connector of said single-use container, (e) a disposable filter between said filtration flow-through section and said filtered fluid section, whereby fluid from said process solution container is filtered through said disposable filter and is collected in said permeate collection container (f) at least one pre-sterilized, calibrated and disposable electrical conductivity sensor adapted for single-time usage, the electrical conductivity sensor senses the electrical conductivity of the biotechnology fluid within the tubing and has a memory component capable of storing data, the memory component including a sensor-specific temperature offset assigned to that specific sensor during calibration of the sensor, wherein said temperature offset was determined during manufacture employing a calibration solution, including determining the actual temperature (Tref) value of the calibration solution, using the specified pre-calibrated sensor to measure the temperature (Tsen) value of the calibration solution, and mathematically combining said Tref and said Tsen into said sensor specific temperature offset, and (g) at least one disposable pressure sensor positioned along said length of tubing such that the biotechnology fluid can flow therethrough at a location selected from the group consisting of upstream, downstream[ah], both upstream and downstream of said disposable filter, and upstream of said outlet end portion; and at least one remotely operable valve, said remotely operable valve engaging said length of tubing and independently selectively allowing or stopping flow of the biotechnology fluid through said inside surface of the length of tubing.

24. The system in accordance with claim 23, wherein said inlet end is within said filtration flow-through section and in operative communication with said process solution single-use container, and said filtration flow-through section further includes a recirculation length of tubing having said valve between an exit port of said disposable filter and said process solution single-use container.

25. The system in accordance with claim 24, wherein the disposable pressure sensor is positioned along said recirculation length of tubing such that the biotechnology fluid can flow therethrough at a location between said disposable filter and said valve along said recirculation length.

26. The system in accordance with claim 23, wherein the disposable pressure sensor is positioned along said tubing such that the biotechnology fluid can flow therethrough at a location upstream of said disposable filter.

27. The system in accordance with claim 23, wherein the disposable pressure sensor is positioned along said filtered fluid length of tubing such that the biotechnology fluid can flow therethrough at a location between said disposable filter and said permeate collection single-use container.

28. The system in accordance with claim 23, wherein said outlet end portion of the tubing has a plurality of serially arranged outlet passageways for respective operable connection with said single-use containers, wherein the disposable filter is positioned such that the biotechnology fluid can flow therethrough at a location upstream of said outlet passageways.

29. The [manifold] system in accordance with claim 23, wherein the container is a bag, and the remotely operable valve is a pinch valve that engages the outside surface of the length of tubing.

30. A manifold and flow imparting system for biotechnology uses, wherein said system is for tangential flow filtration, comprising:

a manifold unit which is pre-sterilized and disposable so as to be adapted for single-time usage, including:

(a) at least one length of tubing having at least one inlet end portion, at least one outlet end portion, an outside surface, and an inside surface which is sterilized for passage of a biotechnology fluid therethrough, (b) a plurality of single-use containers, each having an access port, one said single-use container is a process solution container and another said single-use container is a permeate collection container, (c) said tubing includes at least two sections including a filtration flow-through section and a filtered fluid section, said filtration flow-through section includes said process solution container, said filtered fluid section includes said permeate collection container, (d) an aseptic connector of said single-use container, and (e) a disposable filter between said filtration flow-through section and said filtered fluid section, whereby fluid from said process solution container can be filtered through said disposable filter and can be collected in said permeate collection container, (f) at least one pre-sterilized, calibrated and disposable electrical conductivity sensor adapted for single-time usage, the electrical conductivity sensor senses the electrical conductivity of the biotechnology fluid within the tubing and has a memory component capable of storing data, the memory component including a sensor-specific temperature offset assigned to that specific sensor during calibration of the sensor, wherein said temperature offset was determined during manufacture employing a calibration solution, including determining the actual temperature (Tref) value of the calibration solution, using the specified pre-calibrated sensor to measure the temperature (Tsen) value of the calibration solution, and mathematically combining said Tref and said Tsen into said sensor specific temperature offset, (g) at least one disposable pressure sensor positioned along said length of tubing such that the biotechnology fluid can flow therethrough at a location selected from the group consisting of upstream, downstream, both upstream and downstream of said disposable filter, and upstream of said outlet end portion, and (h) at least one remotely operable valve, the remotely operable valve located so as to engage said length of tubing and independently selectively allowing or stopping flow of the biotechnology fluid through said inside surface of the length of tubing; and a flow imparting unit at a selected location upstream of said disposable filter.

31. The [manifold] system in accordance with claim 30, wherein the container is a bag, and the remotely operable valve is a pinch valve that engages the outside surface of the length of tubing.

32. An automated manifold and flow imparting system for biotechnology uses, wherein said system is for tangential flow filtration, comprising: a manifold unit which is pre-sterilized and disposable so as to be adapted for single-time usage, including: (a) at least one length of tubing having at least one inlet end portion, at least one outlet end portion, an outside surface, and an inside surface which is sterilized for passage of a biotechnology fluid therethrough, (b) a plurality of single-use containers, each having an access port, one said single-use container is a process solution container and another said single-use container is a permeate collection container, (c) said tubing includes at least two sections including a filtration flow-through section and a filtered fluid section, said filtration flow-through section includes said process solution container, said filtered fluid section includes said permeate collection container, (d) a plurality of aseptic connectors of at least one of said single-use containers, (e) a disposable filter between said filtration flow-through section and said filtered fluid section, whereby fluid from said process solution container is filtered through said disposable filter and is collected in said permeate collection container, (f) at least one pre-sterilized, calibrated and disposable electrical conductivity sensor adapted for single-time usage, the electrical conductivity sensor senses the electrical conductivity of the biotechnology fluid within the tubing and has a memory component capable of storing data, the memory component including a sensor-specific temperature offset assigned to that specific sensor during calibration of the sensor, wherein said temperature offset was determined during manufacture employing a calibration solution, including determining the actual temperature (Tref) value of the calibration solution, using the specified pre-calibrated sensor to measure the temperature (Tsen) value of the calibration solution, and mathematically combining said Tref and said Tsen into said sensor specific temperature offset, (g) at least one disposable pressure sensor positioned along said length of tubing such that the biotechnology fluid can flow therethrough at a location selected from the group consisting of upstream, downstream, both upstream and downstream of said disposable filter, and upstream of said outlet end portion, and (h) at least one remotely operable valve, the remotely operable valve engageable with said length of tubing; a flow imparting unit at a selected location upstream of said disposable filter; and a controller operatively controlling said flow imparting unit and said valve, said controller having control logic which [dictates] *is operable to dictate* timing and extent of opening and closing of said remotely operable valve and [dictates] *is operable to dictate* the rate of flow imparted by said flow imparting unit.

33. The automated system in accordance with claim 32, wherein said control logic of the controller [determines] *is operable to determine* the extent of filling of the permeate collection container by processing data monitored by the system to achieve filling of the permeate container by volume, by weight, or by flow rate and filling time.

34. The automated system in accordance with claim 32, wherein the disposable pressure sensor is positioned along a location downstream of said disposable filter for monitoring pressure of the fluid within said tubing and for transmitting data on the pressure to the controller, wherein said control logic receives said data from said disposable pressure sensor and [monitors] *is operable to monitor* the flow of fluid through the filtration flow through section of the tubing until said control logic signals that said filtration flow through section of the tubing is to be blocked by closing one of said remotely operable valves and signals that said filtered fluid section of the tubing is to be unblocked by opening another of said remotely operable valves, whereby filtered fluid begins to flow into said permeate collection container.

35. The automated system in accordance with claim 34, wherein said flow imparting unit has a flow imparting rate and said control logic [directs] *is operable to direct* the flow imparting unit to modify the flow imparting rate in response to changes in pressure at the disposable pressure sensor so as to maintain a selected rate imparted to the fluid by the flow imparting unit.

36. The automated system in accordance with claim 34, further including a fluid flow rate sensor for monitoring fluid velocity, and wherein said control logic [receives] *is operable to receive* fluid velocity data from said fluid flow rate sensor and [processes] *is operable to process* the data for controlling the automated system.

37. The automated system in accordance with claim 36, wherein said flow imparting unit has a flow imparting rate and said control logic [directs] *is operable to direct* the flow imparting unit to modify its the flow imparting rate in response to changes in flow rate at said fluid flow rate sensor so as to maintain a selected flow rate imparted to the fluid by the flow imparting unit.

38. The [manifold] *automated* system in accordance with claim 32, wherein the container is a bag, the remotely operable valve is a remotely operable pinch valve that engages the outside surface of the length of tubing, the flow imparting unit is a pump, and the control logic [controls or dictates] *is operable to control or dictate* the timing of opening and closing of the remotely operable pinch valve.

* * * * *